United States Patent [19]

Virag

[11] 4,034,754

[45] July 12, 1977

[54] INTRAVENOUS SOLUTION SET HAVING A CONSTRICTED INNER DIAMETER PORTION

[75] Inventor: Robert Anthony Virag, Lake Zurich, Ill.

[73] Assignee: Baxter Travenol Laboratories, Inc., Deerfield, Ill.

[21] Appl. No.: 602,614

[22] Filed: Aug. 7, 1975

[51] Int. Cl.² .......................................... A61M 5/00
[52] U.S. Cl. .............................. 128/214 R; 128/221
[58] Field of Search ............ 128/214, 214 C, 214.2, 128/213, 214 E, 214 F, 221, DIG. 13

[56] References Cited

U.S. PATENT DOCUMENTS

| | | | |
|---|---|---|---|
| 3,675,891 | 7/1972 | Reynolds et al. | 128/214 R X |
| 3,677,242 | 7/1972 | Shaye | 128/214 C |
| 3,803,914 | 4/1974 | Noiles | 128/214 C |
| 3,878,869 | 4/1975 | Yamanouchi et al. | 128/214 R X |
| 3,886,937 | 6/1975 | Bobo | 128/214 R |

Primary Examiner—Stephen C. Pellegrino
Attorney, Agent, or Firm—Garrettson Ellis; Paul C. Flattery; John P. Kirby, Jr.

[57] ABSTRACT

A parenteral liquid infusion set comprises flow tubing, and means for connection to blood vessel penetrating means and a parenteral liquid source at opposite ends thereof. A drip chamber is present in the set having a tubular drop-forming member of reduced inner diameter. An intermediately positioned site is present for providing access to the interior of the set from the exterior, the site being positioned downstream from the drip chamber. In accordance with this invention, a portion of the fluid flow tubing downstream from the connection site defines a bore of reduced diameter, when compared with the remainder of the flow tubing, to prevent the creation of a less than atmospheric pressure in the set and to prevent air from being sucked into the flow tubing through an administration set connected at the intermediately positioned site.

16 Claims, 3 Drawing Figures

U.S. Patent   July 12, 1977   4,034,754
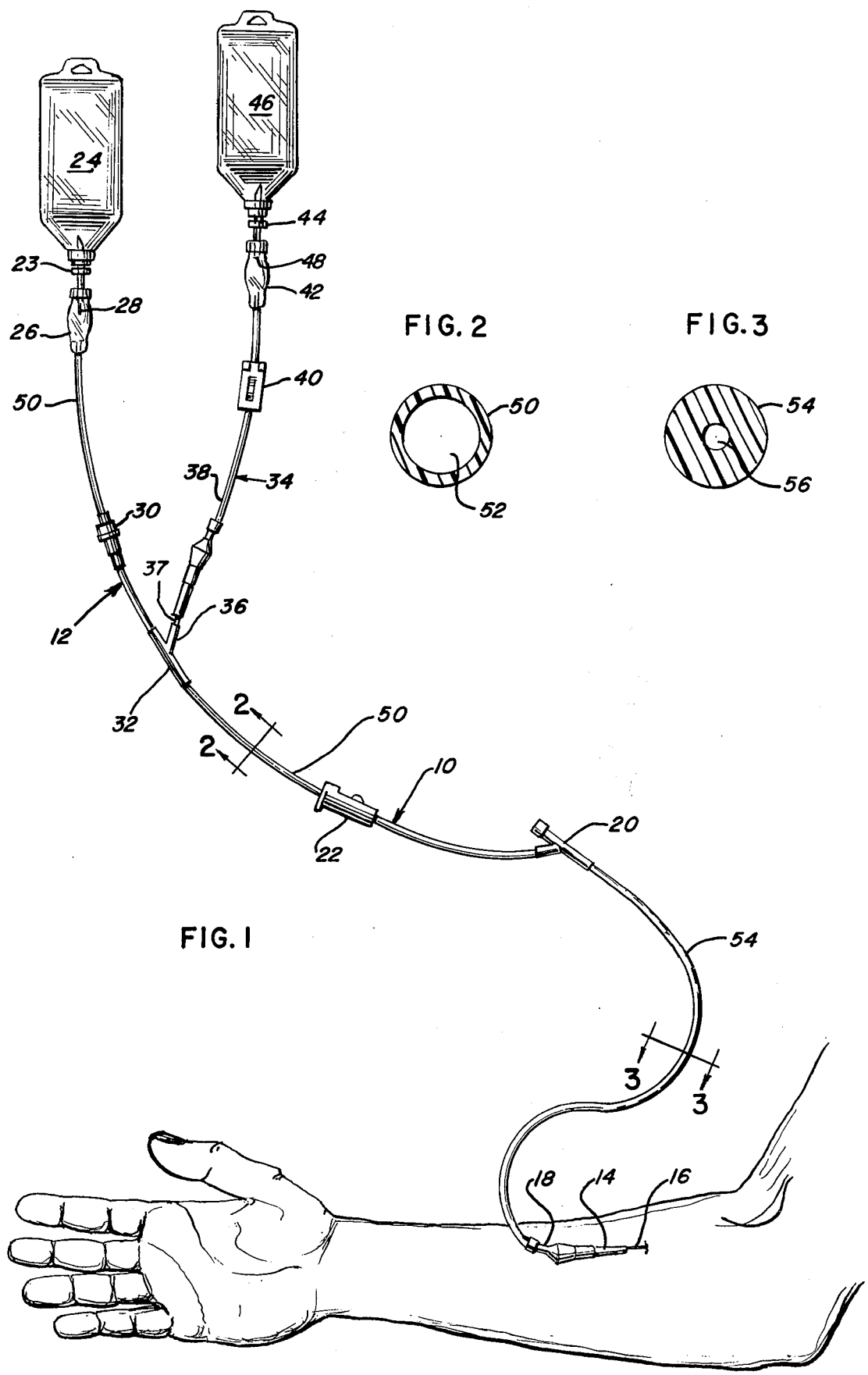

INTRAVENOUS SOLUTION SET HAVING A CONSTRICTED INNER DIAMETER PORTION

BACKGROUND OF THE INVENTION

In the administration of intravenous fluids such as parenteral solutions, physicians frequently desire a connection of two different containers of parenteral solution to the same set, which communicates with a single intravenous needle in communication with the venous system of a patient. For example, the CONTINU-FLO intravenous solution set, sold by Travenol Laboratories, Inc. of Deerfield, Illinois, utilizes fluid flow tubing having a connector on one end for connection with a parenteral solution bag or bottle, and a needle adaptor on its other end for intravenous connection with a patient. A Y-site is positioned on the set, capable of connection with an ADD-A-LINE intravenous solution set, which is also sold by Travenol Laboratories. This latter set is capable of connection at its other end with a second parenteral solution source.

Accordingly, a set-up of the two above-mentioned parenteral solution sets can be used to administer two different solutions. For example, the CONTINU-FLO set may be connected as a first set to a container of normal saline or dextrose solution. The ADD-A-LINE set may be connected, as a second set in connection with the first set, to a container of antibiotic solution. Hence, a slow, continuous drip of normal saline or dextrose may be administered to the patient, for maintenance of an effective parenteral liquid connection with the patient's venous system. This permits the immediate, intermittent administration of the antibiotic as needed over a period of time.

While a continuous drip of normal saline or dextrose solution is required for preventing blood clotting in the needle, it is generally desired for the overall amount of such solution administered on a continuous basis to be very small. In fact, frequently, the desired flow rate can be so low that the conventional drip chamber of an administration set forms drops (about 10 drops per c.c. of fluid administered) which are large enough to fall so infrequently from the drop former of the drip chamber that it becomes difficult and time-consuming to accurately measure the drip rate. Accordingly, the overall fluid administration rate of the set is not easily monitored.

In response to this, parenteral administration sets are sold in which a small drop forming tube is utilized in the drip chamber. This tube may have an inner diameter of typically about 0.02 to 0.03 inch. Such a constricted drop forming chamber in a drip chamber is capable of producing smaller drops, for example, about 60 drops per c.c. of liquid administered. Accordingly, at the same low flow rate, drops of liquid will fall through this drip chamber at a rate six times faster than they would through a large drop forming drip chamber of 10 drops per c.c.

While the above small-drop arrangement is a satisfactory solution for the determination of flow through an administration set at low flow rates, a problem is created in the situation where a pair of solution sources are connected together for intermittent, alternate fluid administration to a patient through a single needle. The problem is that, when a small drop forming member is used in a drip chamber, and a higher overall fluid flow is desired, a suction pressure head can develop in the tubing downstream from the drip chamber. This is so because the small drop forming member may provide an inadequate fluid flow to resupply the set, as solution is administered at a high rate to a patient, impelled by the gravity pressure of the fluid column in the administration set (or alternatively by a pump).

As a result of this, in gravity-operated sets, if the connection site of the second set with the first set is positioned remotely from the patient and near the drip chamber mentioned above, and if the parenteral solution source connected to the second set becomes empty, air may be sucked into the parenteral solution set through the second set. The same event can also take place in pumped sets.

Thereafter, the administration of a second aliquot of solution from the first source of parenteral solution may actually cause air to be forced into the patient, which is extremely undesirable and dangerous. Alternatively, if the presence of air is noticed, the sets may have to be disconnected and reprimed to eliminate air.

The above problem exists whenever an air access site exists in the set, particularly in its upper portion in position of use, where a substantial suction pressure head can form to cause air to be drawn into the set.

While this problem can, in gravity operated sets, be reduced in scope when the access site is positioned lower and nearer to the patient, this can be undesirable, since it brings the site within reach of the patient, and thus is more subject to being tampered with and the like. Furthermore, a downstream connection of primary and secondary sets produces more of a tangle of tubing at the patient's bedside.

The invention of this application overcomes the above difficulties, in that it provides, for the first time, a means whereby an administration set may be safely used with a patient, even though (1) a constricted drop-forming member is used, and (2) an air-access site to the set is vertically elevated, near the drip chamber and the hanging sources of parenteral solution, and away from the patient.

Accordingly, by this invention, the advantages of a constricted drop-forming member of the drip chamber can be achieved, without running the risk of infusing air into the patient. This has hitherto been inherent in the use of such a small-drop drip chamber in conjunction with a connected pair of sets and separate sources of parenteral solution.

DESCRIPTION OF THE INVENTION

The invention of this application relates to a parenteral liquid infusion set which comprises flow tubing, means for connection at one end of the flow tubing with blood vessel penetrating means, and means for connection with a parenteral liquid source at the other end of the tubing. A drip chamber is also provided, having a tubular drop-forming member of reduced inner diameter relative to the normal inner diameter of the flow tubing. An intermediately-positioned air-access site between the exterior and the interior of the set is present, being positioned downstream from the drip chamber in the direction of the set end which is designed to carry the blood vessel penetrating means (such as a needle). This access site may be a sealed connection site for a second set, a porous in-line filter housing, or the like.

In accordance with this invention, a flexible portion of the fluid flow tubing which is positioned downstream from the air-access site, in the direction toward the end which carries the blood vessel penetrating means, defines a bore of reduced diameter, when compared with the bore size of the remainder of the flow tubing. This reduced diameter bore is of a length and diameter sufficient to restrict fluid flow therethrough to such a degree as to prevent the creation of a less than atmospheric pressure in the set between the reduced diameter bore and the tubular, drop-forming member. The reduced diameter bore restricts the flow of solution into the patient to an extent sufficient to permit the reduced inner diameter, tubular, drop-forming member to adequately supply the set with additional solution, thus preventing less than atmospheric pressure conditions from developing downstream of the drop-forming member.

Accordingly, air will not be sucked into the flow tubing through any air-access site such as an administration set connected with an intermediately-positioned connection site, even if such administration set is emptied of solution.

In the drawings,

FIG. 1 is an elevational view of one embodiment of a parenteral fluid infusion set of this invention, shown connected at its respective ends with a first source of parenteral solution and the venous system of the patient, with a second parenteral liquid infusion set and a second source of parenteral liquid being shown in fluid communication with the set of this invention through an intermediately-positioned connection site.

FIG. 2 is an enlarged sectional view of the set of this invention, taken along line 2—2 of FIG. 1.

FIG. 3 is an enlarged sectional view of the set of this invention, taken along line 3—3 of FIG. 1.

Referring to the drawings, set 10 is shown comprising flow tubing 12, which typically may comprise vinyl plastic tubing of a conventional flexible type. A needle adapter 14 is provided at one end of the set, shown in the present embodiment to carry an intravenous needle 16, which, in turn, is shown to be penetrating the venous sytem of a patient. A typical latex blood flashback site 18 is also provided.

An auxiliary, supplementary medication Y-site 20 may be positioned as shown in the set, as well as a roller clamp 22 or another, equivalent clamp for controlling the overall flow of solution to the patient.

At the other end of set 10, a conventional connection spike 23 penetrates a parenteral solution container 24 for access to the contents thereof. Drip chamber 26 is provided, including a tubular, drop-forming member 28, which is typically a metal sleeve having a reduced inner diameter of 0.023 inch in the embodiment shown, to form about 60 drops per c.c. of fluid passing through it.

A one-way valve 30, typically of the duckbill type, is provided as shown to prevent parenteral solution from backing up into container 24.

In the embodiment of FIG. 1, the intermediately positioned site providing potential access of air to the interior of the set from the exterior is a branched connection site of conventional construction for connection with second parenteral solution administration set 34. Prior to connection with set 34, connection site 32 carries a sealing member in arm 36 which seals the set from the exterior, but permits access to the interior by set 34 through access needle or spike 37.

Second set 34 is, as mentioned above, a conventional administration set defined by flexible tubing 38, including roller clamp 40, or any other equivalent flow control means, and drip chamber 42. Piercing spike 44 is shown in connection with a second source of parenteral solution 46.

The drop-forming member 48 of drip chamber 42 may be of any desired inner diameter for forming drops of an appropriate size.

The parenteral solution source 46 is shown to be at an elevated height in position of use with respect to solution source 24, to provide an increased pressure head through set 34. It is for this reason that one-way valve 30 is present, to prevent solution from set 34 from passing upwardly toward first parenteral solution source 24 when clamp 40 is opened.

In accordance with this invention, a first, upper length of tubing 50 of set 10 has a relatively and conventionally large diameter of bore 52, as shown in FIG. 2, for example from 0.05 to 0.15 inch in diameter, and specifically 0.10 inch in diameter. Such conventional tubing may have a wall thickness of about 0.01 to 0.025 inch, the preferred wall thickness being about 0.019 inch.

Another length of tubing 54 of set 10 defines a bore 56 of restricted diameter, as shown in FIG. 3. This length of flexible tubing 54 is at least two and preferably at least 5 inches in length, and defines a bore of about 0.01 inch to 0.04 inch in diameter. As a specific example, tube section 54 may be 24 inches in length and may define a bore 56 having a diameter of 0.028 inch. Tubing 54 may be colored for identification.

As a result, the overall flow through set 10 is restricted by the length of tubing 54 to a degree necessary to prevent the creation of a less than atmospheric pressure in the vicinity of connection site 32, caused by gravity suction produced by the column of liquid in the set below connection site 32, when, for example, clamp 22 is in wide open configuration. Without tubing 54, if such a subatmospheric pressure were allowed to be created, when container 46 runs dry, it would be possible for air to pass through set 34 into set 10 if clamp 22 remains in the open position. The air could then be driven into the patient by the weight of additional parenteral solution from solution source 24, overcoming the venous pressure of the patient, and forcing air bubbles into the patient.

When a properly proportioned section of constricted tubing 54 is provided, such a reduced pressure cannot be created, and accordingly air is not sucked into the set through site 32. The appropriate amount of flow restriction can be easily controlled by lengthening or shortening tubing 54. This correspondingly increases or reduces the flow restriction without the need to replace tubing 54 with tubing having a different bore size.

Also, tube section 54 reduces the possibility of accidentally "flooding" the patient with an excessive inflow of parenteral solution. Furthermore, sets utilizing this invention can be flow-controlled by changing the elevation of containers 24, 46.

As a further advantage, tubing 54, preferably having an increased wall thickness of about 0.04 to 0.08 inch, and typically about 0.057 inch, does not as easily kink when placed in U-shaped configuration on the patient's arm, when compared with conventional tubing.

If desired, site 32 can be replaced with a venting, in-line filter type device, for the removal of air from administration sets. Also, site 32 can be replaced with any other connection site providing the possibility of air-access, such as a T-shaped site, a latex injection bulb, filter housings with integral injection sites, or preattached supplemental medication sets like set 34.

The above has been offered for illustrative purposes only, and is not for the purpose of restricting the scope of the invention of this application, which is as defined in the claims below.

That which is claimed is:

1. In a parenteral liquid infusion set which comprises flexible flow tubing, means for connection at one end of said flow tubing with blood vessel penetrating means, means for connection with a parenteral liquid source at the other end of said tubing, drip chamber means having a tubular drop-forming member at an upper end thereof of reduced inner diameter of 0.02 to 0.03 inch relative to the inner diameter of said flow tubing, and an intermediately-positioned site providing potential access of air to the interior of said set from the exterior, said site being positioned downstream from said drip chamber, but in the upper portion of the set, the improvement comprising, in combination: an integrally attached portion of said flexible fluid flow tubing positioned downstream from said access site defining a bore of reduced diameter, when compared with the bore size of the remainder of said flow tubing, said reduced diameter bore being from 0.01 to 0.04 inch in diameter and at least two inches in length, said reduced diameter bore being proportioned to prevent the creation of less than atmospheric pressure in said set between said reduced diameter bore and said drop-forming member in normal use, to prevent air from being sucked into said flow tubing through said inter-mediately-positioned axis site.

2. The infusion set of claim 1 in which said access site includes means for forming a connection with another parenteral liquid infusion set.

3. The infusion set of claim 2 in which said intermediately-positioned connection site is in fluid communication with one end of a second parenteral liquid infusion set, said second set comprising tubing, the other end of said second set being adapted for fluid communication with a parenteral liquid source.

4. The infusion set of claim 3, which comprises a one-way valve positioned between said intermediately positioned connection site and said means for connection with a parenteral liquid source, said one-way valve being positioned to permit flow from said parenteral source connection means toward said intermediately positioned connection site.

5. The infusion set of claim 1 in which said access site is a connection site for forming a connection with a second parenteral liquid infusion set.

6. The infusion set of claim 5 in which the wall thickness of said tubing portion of reduced bore diameter is from 0.04 to 0.08 inch, and greater than the wall thickness of the remainder of said flow tubing, to reduce kinking.

7. The parenteral liquid infusion set of claim 6, in which each said set is respectively in connection with first and second sources of parenteral liquid, said second source of parenteral liquid being in connection with said second set, and being vertically higher than the first source of parenteral liquid, to provide preferential flow out of said second source of parenteral liquid through said second set when said flow is permitted.

8. The infusion set of claim 1 in which said flow tubing of reduced diameter bore exhibits a wall thickness of 0.04 to 0.08 inch.

9. The infusion set of claim 8 in which said tubing of reduced diameter bore is at least 5 inches in length.

10. In a parenteral liquid infusion set which comprises flexible flow flow tubing, means for connection at one end of said flow tubing with blood vessel penetrating means, means for connection with a parenteral liquid source at the other end of said tubing, and means, positioned intermediately on said infusion set, for the addition of supplemental medication, the improvement comprising, in combination:

the tubing which extends between said blood vessel connection means at one end of the flow tubing and said means for the addition of supplemental medication defines a bore having a diameter of 0.01 to 0.04 inch, and further defines a wall thickness of 0.04 to 0.08 inch, whereby said tubing is resistant to kinking, the length of said tubing which extends between said blood vessel connection means and the means for the addition of supplemental medication being at least 5 inches, the diameter of the bore of the major portion of the tubing in said parenteral liquid infusion set being greater than the diameter of said tubing which extends between the connection means and the supplemental medication addition means.

11. The infusion set of claim 10 in which the tubing upstream of said supplemental medication addition means between said addition means and said parenteral liquid source connection means defines a bore of 0.05 to 0.15 inch in diameter.

12. The infusion set of claim 11 in which said upstream tubing defines a wall thickness of from 0.01 to 0.025 inch.

13. In a parenteral liquid infusion set which comprises flexible flow tubing, means for connection at one end of said flow tubing with blood vessel penetrating means, means for connection with a parenteral liquid source at the other end of said tubing, an intermediately-positioned site providing potential access of air to the interior of said set from the exterior, and means positioned intermediately on said infusion set for the addition of supplemental medication, the improvement comprising, in combination:

the tubing which extends between said blood vessel connection means at one end of the flow tubing and said supplemental medication addition means defining a reduced diameter bore of 0.01 to 0.04 inch in diameter, said tubing of reduced diameter bore being at least 5 inches in length and defining a wall having a thickness of from 0.04 to 0.08 inch.

14. In a parenteral liquid infusion set which comprises flexible flow tubing, means for connection at one end of said flow tubing with blood vessel penetrating means, means for connection with a parenteral liquid source at the other end of said tubing, and means positioned intermediately on said infusion set for the addition of supplemental medication, the improvement comprising, in combination:

the tubing extending between said blood vessel connection means at one end of the flow tubing and said supplemental medication addition means defining a reduced diameter bore of 0.01 to 0.04 inch in diameter, said tubing of reduced diameter bore being at least 2 inches in length and defining a bore which is smaller than the remainder of said flexible flow tubing in the parenteral liquid infusion set, and having a wall thickness which is greater than the wall thickness of the remainder of the flexible flow tubing in said parenteral infusion set.

15. The parenteral liquid infusion set of claim 14 in which the length of said tubing of reduced diameter bore is at least 5 inches.

16. In a parenteral liquid infusion set which comprises flexible flow tubing, means for connection at one end of said flow tubing with blood vessel penetrating means, means for connection with a parenteral liquid source at the other end of said tubing, drip chamber means having a tubular, drop-forming member at an upper end thereof of reduced inner diameter relative to the inner diameter of said flow tubing, and an intermediately positioned site providing potential access of air to the interior of said set from the exterior, said site being positioned downstream from said drip chamber, the improvement comprising, in combination: a portion of said flexible fluid flow tubing positioned downstream from said access site defining a bore of reduced diameter, when compared with the bore size of the remainder of said flow tubing, said reduced diameter bore being from 0.01 to 0.04 inch in diameter and at least 2 inches in length, said bore being proportioned to prevent the creation of less than atmospheric pressure in said set between said reduced diameter bore and said drop-forming member in normal use, to prevent air from being sucked into said flow tubing to said intermediately-positioned access site, said tubing of reduced diameter bore having a greater wall thickness when compared with the wall thickness of the major portion of said flexible fluid flow tubing.

* * * * *